(12) United States Patent
Meoni

(10) Patent No.: US 11,124,324 B2
(45) Date of Patent: Sep. 21, 2021

(54) PROCESS OF STERILIZATION OF A PACKAGING SYSTEM, AND ELEMENT FOR CLOSING THE INTERFACE OPENING BETWEEN AN APPARATUS FOR STERILIZING CONTAINERS AND A FILLING MACHINE

(71) Applicant: I.M.A. INDUSTRIA MACCHINE AUTOMATICHE S.P.A IN SIGLA IMA S.P.A., Ozzano Dell'Emilia (IT)

(72) Inventor: Eddi Meoni, Ozzano Dell'Emilia (IT)

(73) Assignee: I.M.A. INDUSTRIA MACCHINE AUTOMATICHE S.P.A IN SIGLA IMA S.P.A., Ozzano Dell'Emilia (IT)

( * ) Notice: Subject to any disclaimer, the term of this patent is extended or adjusted under 35 U.S.C. 154(b) by 296 days.

(21) Appl. No.: 16/085,735

(22) PCT Filed: Mar. 16, 2017

(86) PCT No.: PCT/EP2017/056293
§ 371 (c)(1),
(2) Date: Sep. 17, 2018

(87) PCT Pub. No.: WO2017/158118
PCT Pub. Date: Sep. 21, 2017

(65) Prior Publication Data
US 2019/0084711 A1    Mar. 21, 2019

(30) Foreign Application Priority Data

Mar. 17, 2016    (IT) ..................... 102016000027985

(51) Int. Cl.
*B65B 55/10*    (2006.01)
*A61L 2/20*    (2006.01)
(Continued)

(52) U.S. Cl.
CPC ............... *B65B 55/10* (2013.01); *A61L 2/00* (2013.01); *A61L 2/208* (2013.01); *B65B 35/30* (2013.01);
(Continued)

(58) Field of Classification Search
CPC ..... B65B 55/04; B65B 55/10; B65B 2210/06; B65B 2210/08; B65B 65/003; B65B 35/30; A61L 2202/121; A61L 2/00; A61L 2/208
See application file for complete search history.

(56) References Cited

U.S. PATENT DOCUMENTS

| 3,681,008 A | * | 8/1972 | Black | ................. A61L 2/26 422/117 |
| 5,022,165 A | * | 6/1991 | Beswick | ............... B65B 55/10 34/105 |
| 2014/0301895 A1 | * | 10/2014 | Opie | .................. A61L 2/26 422/28 |

FOREIGN PATENT DOCUMENTS

| DE | 19726222 A1 | 12/1998 |
| DE | 19817735 C1 | 11/1999 |
| EP | 0570946 A1 | 11/1993 |

OTHER PUBLICATIONS

International Search Report dated May 18, 2017 re: Application No. PCT/EP2017/056293, pp. 1-4.
(Continued)

*Primary Examiner* — Anna K Kinsaul
*Assistant Examiner* — Veronica Martin
(74) *Attorney, Agent, or Firm* — Cantor Colburn LLP

(57) ABSTRACT

A process of sterilization of a packaging system, constituted by an apparatus for sterilizing containers and by a filling machine, which includes arranging a door so as to close the interface opening defined between the apparatus for sterilizing containers and the filling machine, at least two expand-
(Continued)

able gaskets, each closed onto itself, being interposed between the door and the opening and coupled to a perimetric region of a component chosen from either the door or the delimiting edge of the opening. In subjecting the apparatus to sterilization, keeping inactive, therefore with minimum space occupation and separated from the door, the gasket that lies closest to the apparatus and keeping expanded, therefore with maximum space occupation and in hermetic abutment against the door, the gasket that lies furthest from the apparatus.

10 Claims, 6 Drawing Sheets

(51) Int. Cl.
  *B65B 35/30* (2006.01)
  *B65B 65/00* (2006.01)
  *A61L 2/00* (2006.01)

(52) U.S. Cl.
  CPC ........ *B65B 65/003* (2013.01); *B65B 2210/06* (2013.01)

(56) References Cited

OTHER PUBLICATIONS

IT Search Report dated Nov. 25, 2016 re: Application No. IT UA20161756, pp. 1-7.
Written Opinion dated May 18, 2017 re: Application No. PCT/EP2017/056293, pp. 1-4.

\* cited by examiner

PROCESS OF STERILIZATION OF A PACKAGING SYSTEM, AND ELEMENT FOR CLOSING THE INTERFACE OPENING BETWEEN AN APPARATUS FOR STERILIZING CONTAINERS AND A FILLING MACHINE

TECHNICAL FIELD

The present disclosure relates to a process of sterilization of a packaging system, and to an element for closing the interface opening between an apparatus for sterilizing containers and a filling machine.

BACKGROUND

In some industrial sectors (in particular the pharmaceutical sector, but also, in some cases in the food industry, in the cosmetics industry etc.) it is necessary to sterilize the containers that will subsequently be filled with the product (of interest to the end user).

The aim of the preliminary sterilization of the containers is linked to the need to not contaminate in any way the product with which they will be filled.

For this reason, there is a step of sterilization in which the sterilization is carried out of the entire sterilization apparatus (in particular its internal chamber within which the containers are conveyed) and of the filling machine (in this case too concentrating on just the area within which the containers or the product are conveyed). The combination of the sterilization apparatus and the filling machine constitutes a packaging system.

Usually in sterilization apparatuses, a high temperature is created inside the chamber for conveying the containers, in order to eliminate the contaminants.

In particular the apparatuses comprise an entry station of the containers (which does not need to be subjected to sterilization), a sterilization station (within which the containers are subjected to elevate temperatures) and a cooling station (in which the containers are returned to temperatures suitable to their subsequent filling).

In a preliminary step before putting the sterilization apparatus into operation, it is necessary that the cooling station also be subjected to high temperatures, in order to ensure that the containers, inside it, cannot in any way be contaminated.

In order to allow the creation of the necessary sterilization temperature in the cooling station, the opening from such station through which the containers exit is closed (this is the opening connected to the entry to the filling machine, arranged downstream) using an adapted closure door.

Similarly, the filling machines also need to be subjected to a preliminary sterilization treatment, so as to eliminate and/or inertize all the potentially contaminant residues present inside them.

In particular the use is known of VHP (Vaporized Hydrogen Peroxide), diffused inside the machine, in order to execute these sterilization operations.

In order to prevent leaks of the sterilization vapors, and their entry into the cooling station of the sterilization apparatus arranged upstream (through the connection opening), the door to close the sterilization apparatus makes it possible to segregate the internal volume of the filling machine as well (by delimiting the volume in which the hydrogen peroxide vapors can circulate).

It is clear that, by virtue of these operations, it is possible to carry out an accurate sterilization of the entire packaging line.

In reality however, there is one area that is not subjected to any sterilization: this is an edge of the opening on which the closure door is overlaid.

The door will in fact be characterized by a surface juxtaposed with the aforementioned edge of the opening, with the interposition of a specific gasket, in order to ensure the temporary mutual isolation of the sterilization apparatus and of the filling machine.

It is therefore evident that the sterilization operations will be effective upstream and downstream of the gasket of the door, while the portion of opening that is juxtaposed with the gasket will not undergo any sterilization and may therefore comprise some contaminant substances.

SUMMARY

The aim of the present disclosure is to solve the above mentioned drawbacks, by providing a process of sterilization of a packaging system that extends to all the parts and the components facing the conveyance path of the containers.

Within this aim, the disclosure provides an element for closing the interface opening between an apparatus for sterilizing containers and a filling machine that makes it possible to subject every part of the apparatus and of the machine to sterilization operations and, in particular, the entire surface of the edges delimiting the opening.

The present disclosure also provides an element for closing the interface opening between an apparatus for sterilizing containers and a filling machine that enables the execution of extraordinary sterilization operations of the apparatus and of the machine in the traditional manner.

The disclosure further provides an element for closing the interface opening between an apparatus for sterilizing containers and a filling machine in which the shape, technical structure and operation are substantially different from those of conventional packaging systems.

The present disclosure provides an element for closing the interface opening between an apparatus for sterilizing containers and a filling machine, which are low cost, easily and practically implemented, and safe in use.

This aim and these and other advantages which will become better apparent hereinafter are achieved by providing a process of sterilization of a packaging system, constituted by an apparatus for sterilizing containers and by a filling machine, which comprises:

arranging a door so as to close the interface opening defined between said apparatus for sterilizing containers and said filling machine, at least two expandable gaskets, each closed onto itself, being interposed between said door and said opening and coupled to a perimetric region of a component chosen from either said door or the delimiting edge of said opening, subjecting said sterilization apparatus to sterilization, keeping inactive, therefore with minimum space occupation and separated from said door, the gasket that lies closest to said apparatus and keeping expanded, therefore with maximum space occupation and in hermetic abutment against said door, the gasket that lies furthest from said apparatus, subjecting said filling machine to sterilization, keeping inactive, therefore with minimum space occupation and separated from said door, the gasket that lies closest to said machine and keeping expanded, therefore with maximum space occupation and in hermetic abutment against said door, the gasket that lies furthest from said machine.

Such aim and such advantages are also achieved by providing an element for closing the interface opening between an apparatus for sterilizing containers and a filling machine, characterized in that it comprises a door, which can move between a first configuration of juxtaposition and closure of said opening and a second configuration of misalignment and opening of said opening, between said door and the edge of said opening, and juxtaposed therewith in said first configuration, there being interposed and coupled to a perimetric region of a component chosen from either said door or the delimiting edge of said opening at least two continuous and closed perimetric gaskets, which delimit said opening, each gasket being expandable independently, upon the expansion of at least one first gasket, at least one second gasket, not subjected to expansion, being connected to the internal compartment of either said sterilization apparatus or said filling machine, therefore undergoing the respective sterilization treatment simultaneously with said compartment.

BRIEF DESCRIPTION OF THE DRAWINGS

Further characteristics and advantages of the disclosure will become better apparent from the detailed description that follows of a preferred, but not exclusive, embodiment of the process of sterilization of a packaging system and of the element for closing the interface opening between an apparatus for sterilizing containers and a filling machine according to the disclosure, which is illustrated by way of non-limiting example in the accompanying drawings, wherein.

DETAILED DESCRIPTION OF THE DRAWINGS

Figure 1:
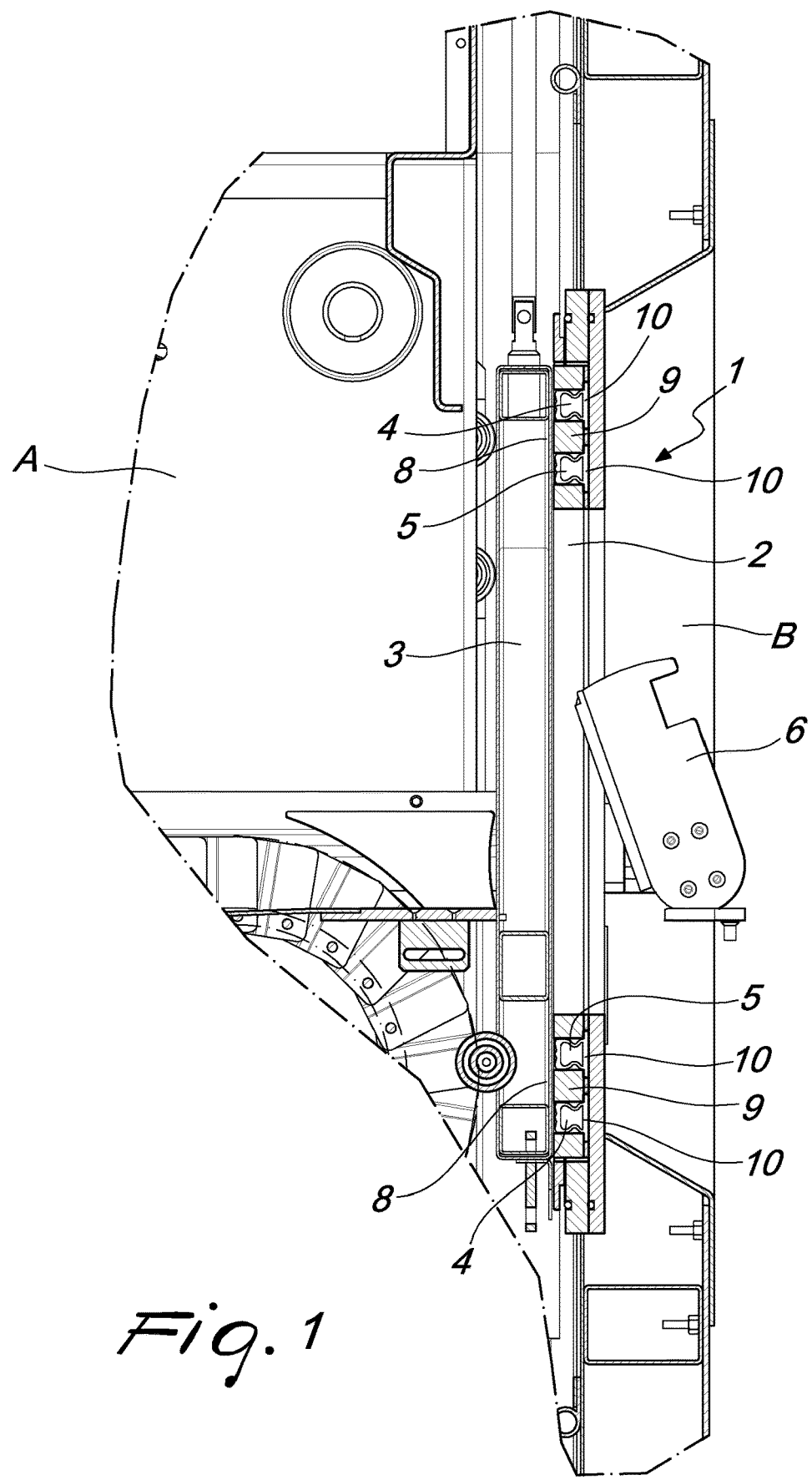
FIG. 1 is a cross-sectional side view taken along a transverse plane of a connection area defined between a sterilization apparatus and a filling machine, which comprises an interface opening on which a closing element according to the disclosure is overlaid.

With reference to the figures, an element for closing the interface opening 2 between an apparatus A for sterilizing containers C and a filling machine B is generally designated by the reference numeral 1: the sterilization apparatus A and the filling machine B constitute a packaging system.

According to the disclosure, the innovative sterilization process of a packaging system entails a series of consecutive steps intended to ensure an optimal sterilization of all the parts of the plant through which the containers C can pass (with the aim of preventing them from being subjected to a contaminant agent during the steps of packaging).

Firstly it is necessary to arrange a door 3 so as to close the interface opening 2, defined between the sterilization apparatus A and the filling machine B.

At least two expandable gaskets 4 and 5, each closed onto itself, are interposed between the door 3 and the opening 2 and coupled to a perimetric region of a component chosen from either the door 3 or the delimiting edge of the opening.

It is then necessary to subject the sterilization apparatus A to sterilization, keeping inactive, therefore with minimum space occupation and separated from the door 3, the gasket 4 that lies closest to the apparatus A. In this step the gasket 5, i.e. the one that lies furthest from the apparatus A, will instead be expanded, therefore with maximum space occupation: such condition will determine the abutment of the (expanded) gasket 5 against the door 3 so as to define a mutual hermetic mating.

During this step of sterilization of the apparatus A, the temperature inside the apparatus A will be increased to extremely high levels (at least higher than 100° C., and often far higher). The high-temperature air inside the apparatus A can circulate freely in the entire volume inside it and can also strike the surface of the door 3 that faces and is proximate to the inactive gasket 4.

In this manner, during the sterilization of the apparatus A, the sterilization will also occur of the inactive gasket 4 and also of the parts of the door 3 and opening 2 that are arranged upstream of the gasket 5 (which ensures the hermetic closure of the apparatus A proper).

Subsequently, it will become necessary to subject the filling machine B to sterilization, keeping inactive, therefore with minimum space occupation and separated from the door 3, the gasket 5 that lies closest to the machine B and keeping expanded, therefore with maximum space occupation and in hermetic abutment against the door, the gasket 4 that lies furthest from the machine B.

During this step of sterilization of the machine B, VHP (vaporized hydrogen peroxide) is diffused inside the machine B. Such vapors, present inside the machine B, can circulate freely in the entire volume inside it and can also strike the surface of the door 3 that faces and is proximate to the inactive gasket 5.

In this manner, during the sterilization of the machine B, the sterilization will also occur of the inactive gasket 5 and also of the parts of the door 3 and opening 2 that are arranged upstream of the gasket 4 (which ensures the hermetic closure of the apparatus A proper).

In the transition from the step of sterilizing the apparatus A to the step of sterilizing the machine B, there is an intermediate step in which both the gaskets 4 and 5 will be in the expanded configuration.

Both the gaskets 4 and 5 can return to the inactive configuration which corresponds to the minimum space occupation, only at the end of both steps of sterilization: at this point it will also be possible to remove the door 3 in order to reopen the opening 2.

According to a specific form of execution of the process according to the disclosure, the expansion of the gaskets 4 and 5 can positively be obtained by way of the independent inflation thereof. In such case, it will be necessary to have a respective pneumatic supply circuit controlled by way of a solenoid valve (or other component equivalent thereto) which is controlled by a control and management unit.

It should be noted that the apparatus A for sterilizing the containers C and the machine B are separate devices: the conveyance path for the containers C therefore necessarily has a point of discontinuity between the apparatus A and the machine B.

In order to allow the easy conveyance of the containers C from the apparatus A to the machine B, there is a guide bridge 6 that can be juxtaposed to the area of discontinuity of the conveyance paths defined respectively on the apparatus A and on the machine B.

When a sterilization needs to be carried out of the apparatus A and of the machine B, it is necessary to have a preliminary step of interrupting the conveyance path of the containers C, which includes removing the guide bridge 6 (designed to form an interconnection between the portion of the conveyance path that is inside the apparatus A and is terminal with respect to it and the portion of the conveyance path that is inside the machine B and is initial with respect to it).

The process according to the disclosure is briefly illustrated in FIGS. 2 to 6 accompanying this application.

Figure 2:
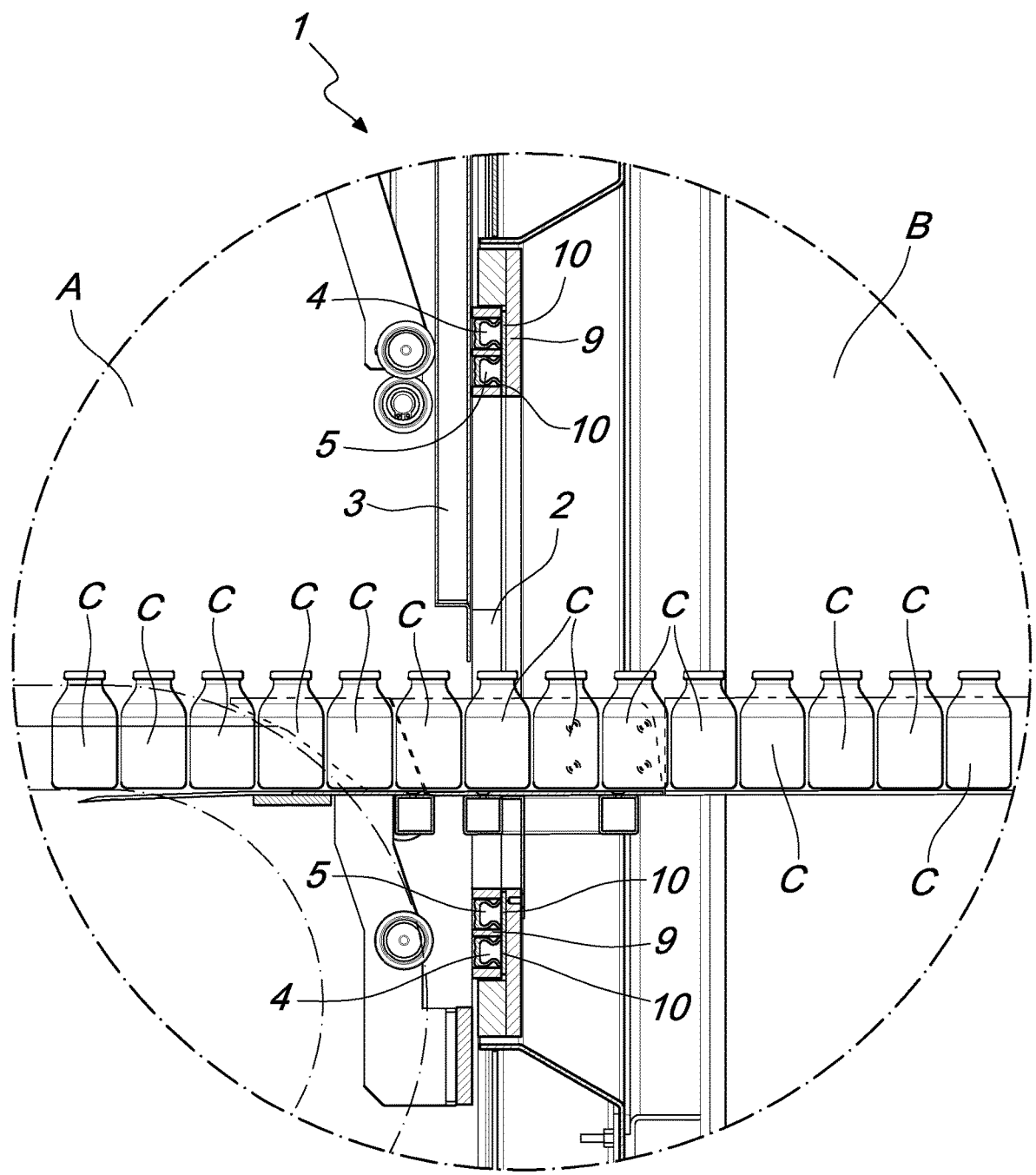
FIG. 2 is a schematic cross-sectional side view taken along a transverse plane of the flow of sterilized containers between a sterilization apparatus and a filling machine.

FIG. 2 illustrates a standard step of operation of the packaging system in which the containers C, after having been subjected to sterilization in the apparatus A, move past the opening 2 (by sliding along the guide bridge 6) and arrive at the filling machine B inside which they will be filled with a specific product (for example a medicine).

Figure 3:
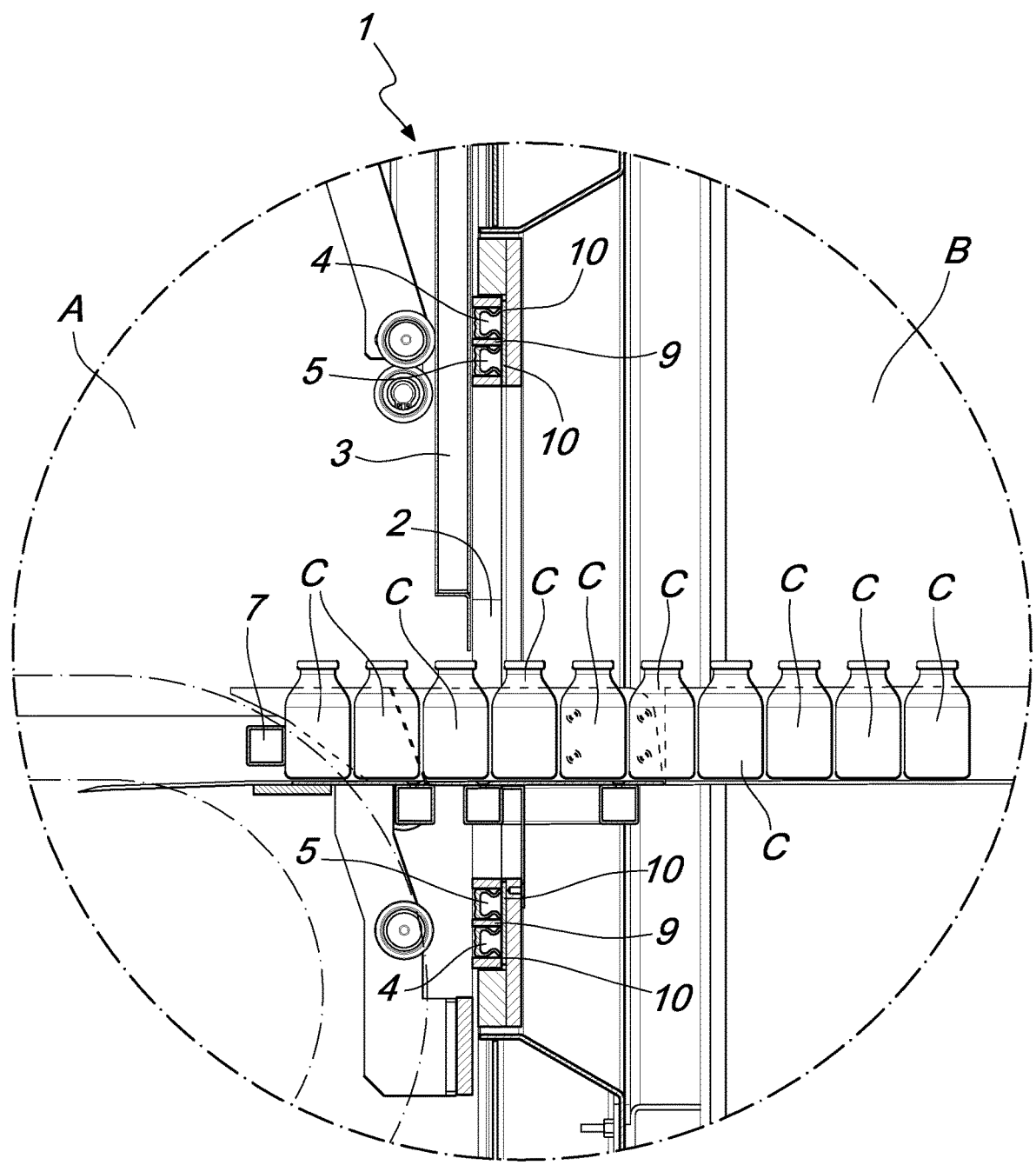
FIG. 3 is a schematic cross-sectional side view taken along a transverse plane of the step of interrupting the flow of sterilized containers between a sterilization apparatus and a filling machine.

FIG. 3 shows the interruption of the flow of containers C, for example as a consequence of the necessity to intervene in the system for maintenance operations.

It is useful to highlight that, when the containers C leave the active conveyor inside the apparatus A they are no longer able to advance on their own toward the station B (the guide bridge 6 does not comprise any drive unit).

The use is therefore known of a pusher 7 that will transfer the containers C along the guide bridge 6, up to the machine B.

Once all the containers C have been processed, it will be possible to interrupt the operation of the packaging system, and this can also correspond to the interruption of the movement of the conveyance path (both the part inside the apparatus A and the part inside the machine B).

Figure 4:
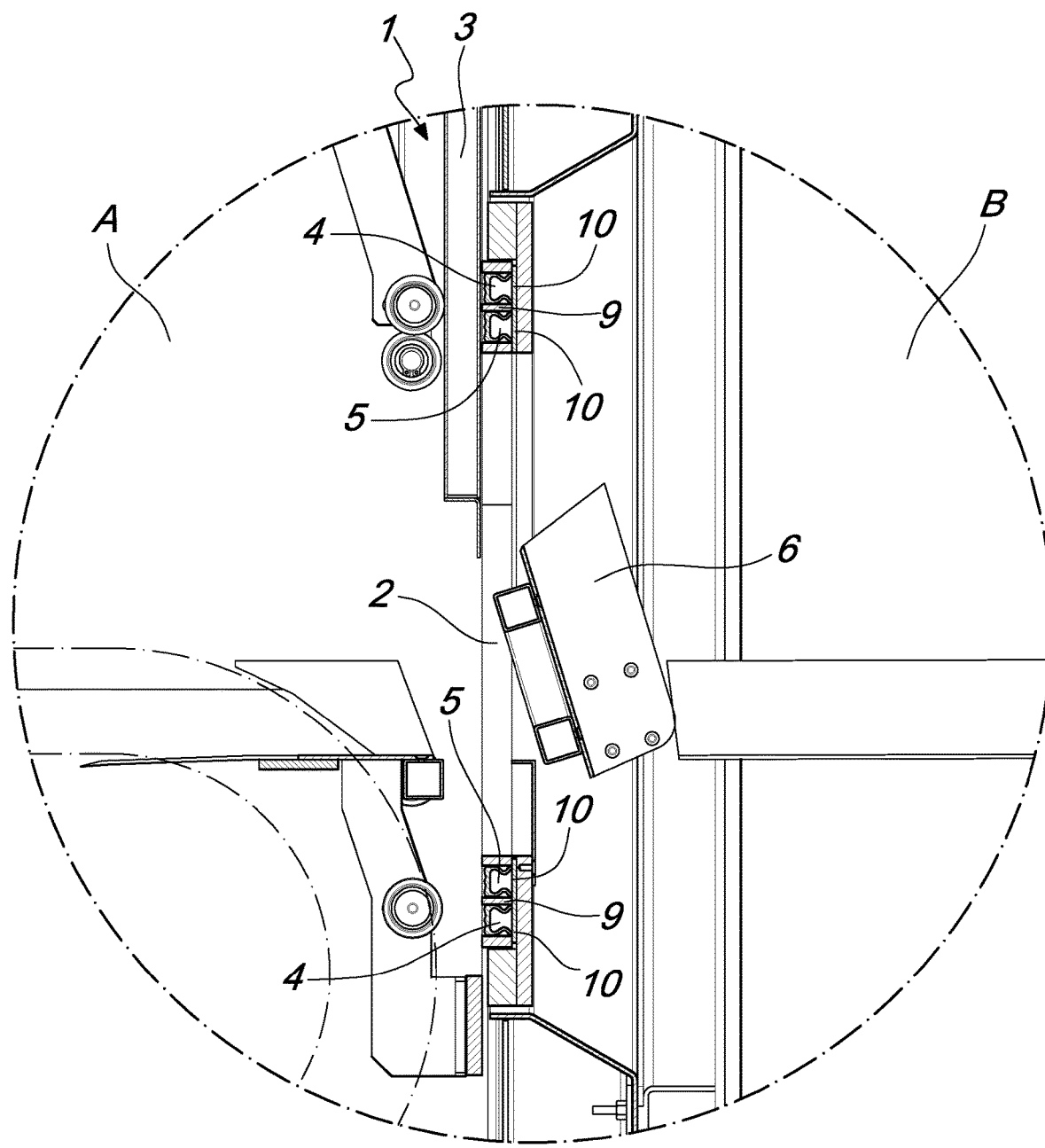
FIG. 4 is a schematic cross-sectional side view taken along a transverse plane of the step of interrupting the conveyance path of the containers between a sterilization apparatus and a filling machine.

In FIG. 4 it can be seen that, having reached this point, it will be possible to move the guide bridge 6, thus producing a discontinuity in the conveyance path (between the part inside the apparatus A and the part inside the machine B).

Figure 5:
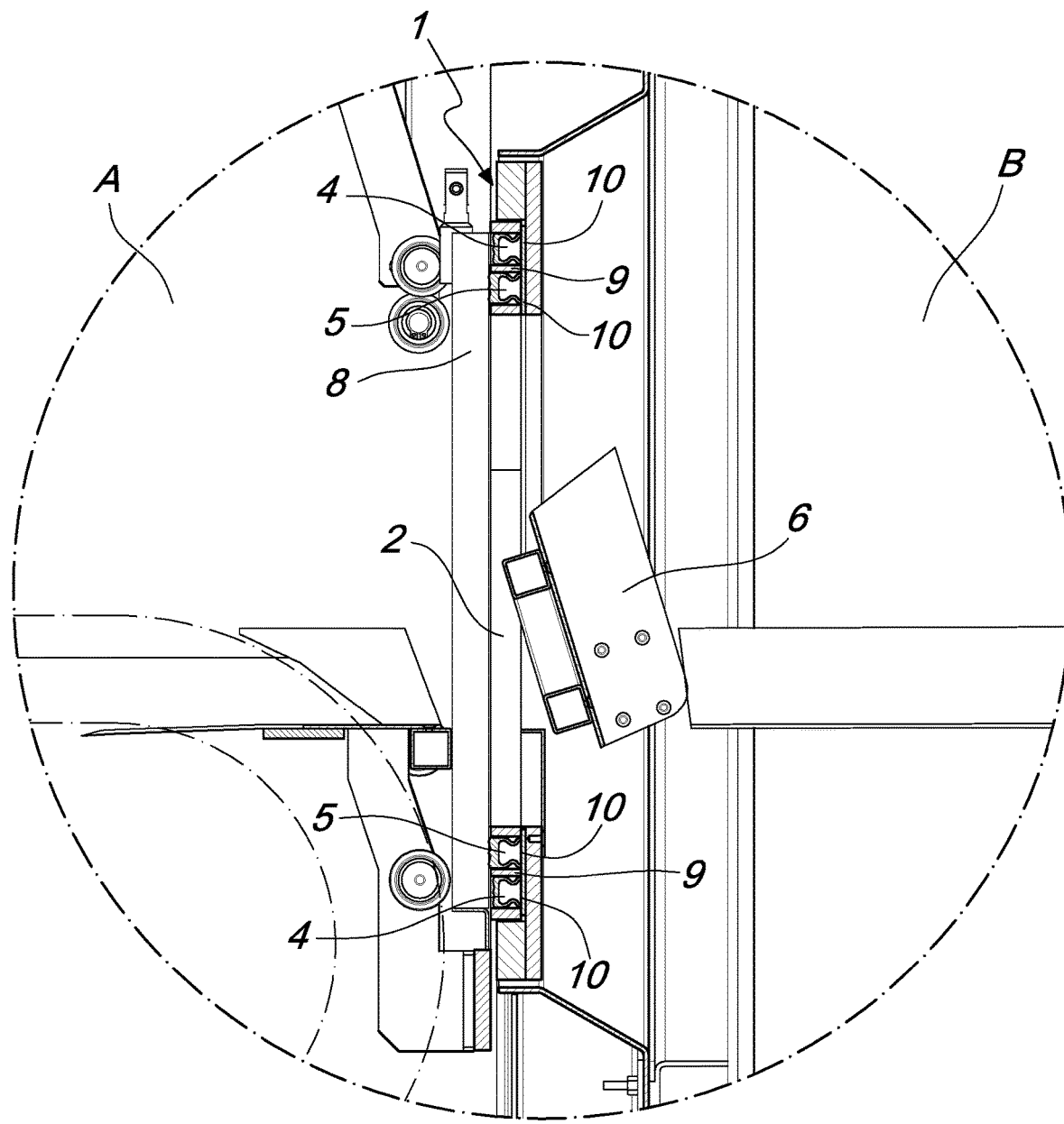
FIG. 5 is a schematic cross-sectional side view taken along a transverse plane of the step of closing the opening between a sterilization apparatus and a filling machine in order to carry out the sterilization of the sterilization apparatus.

FIG. 5 shows the step of sterilizing the apparatus A.

Firstly it should be noted that the door 3 is in the configuration to close the opening 2: it is possible to see that the gasket 4 (outermost, and closest to the apparatus A) is in the inactive condition (minimum space occupation and separated from the door 3) while the gasket 5 (innermost, and furthest from the apparatus A) is expanded (maximum space occupation and in hermetic abutment against the door 3).

The hot air found inside the apparatus A during its sterilization can therefore flow from the outline of the door 3 along its face directed toward the machine B, and strike the inactive gasket 4 and the outer surface of the expanded gasket 5, as well as the parts of the door 3 and the edge of the opening 2 that are delimited between the gaskets 4 and 5.

Once sterilization of the apparatus A has finished, the expansion of the gasket 4 will be begun.

FIG. 5 shows the step of sterilizing the machine B, in which the gasket 5 (innermost, and closest to the machine B) is in the inactive condition (minimum space occupation and separated from the door 3) while the gasket 4 (outermost, and furthest from the machine B) is expanded (maximum space occupation and in hermetic abutment against the door 3).

The hydrogen peroxide vapors that are found inside the machine B during the sterilization thereof can therefore flow from the outline of the door 3 also along its face directed toward the apparatus A, and strike the inactive gasket 5 and the outer surface of the expanded gasket 4, as well as the parts of the door 3 and the edge of the opening 2 that are delimited between the gaskets 4 and 5.

In this manner, it has been seen that the process of sterilization according to the disclosure makes it possible to eliminate the risks of contamination on every part of the packaging system and, in particular, also on the door 3 and on the portions of the opening 2 that are proximate thereto (as well as on the gaskets 4 and 5).

The present disclosure also relates to an innovative element 1 for closing the interface opening 2 between an apparatus A for sterilizing containers C and a filling machine B that makes it possible to optimize the sterilization operations.

The element 1 according to the disclosure comprises a door 3, which can move between a first configuration of juxtaposition and closure of the opening 2 (visible by way of example in the accompanying FIGS. 1, 5 and 6) and a second configuration of misalignment and opening of the opening 2 (visible by way of example in the accompanying FIGS. 2, 3 and 4).

Between the door 3 and the edge of the opening 2, which are mutually juxtaposed in the first configuration (visible by way of example in the accompanying FIGS. 1, 5 and 6), at least two continuous and closed perimetric gaskets 4 and 5 are interposed.

The gaskets 4 and 5 delimit the opening 2: each gasket 4 and 5 is independently expandable.

Upon the expansion of at least one first gasket 4 or 5, at least one second gasket 5 or 4, not subjected to expansion, will be conveniently connected to the internal compartment of either the sterilization apparatus A or the filling machine B, therefore undergoing the respective sterilization treatment simultaneously with such compartment.

It is useful to point out that the expandable gaskets 4 and 5 are inflatable: the respective inflation will be done by a respective pneumatic supply circuit controlled by a respective control and management unit (not shown in the accompanying figures).

According to a specific embodiment of undoubted applicative interest, the door 3 can positively be slideable parallel to the opening 2: such embodiment is the one shown by way of example in the accompanying figures.

In the first configuration of juxtaposition and closure of the opening 2, the perimetric frame 8 of the door 3 will be aligned and proximate to the edge 9 of the opening 2.

The expandable gaskets 4 and 5 will be one inside the other (with a geometric shape structure substantially complementary to that of the opening 2 proper); the gaskets 4 and 5 will be arranged substantially along the perimeter of the opening 2 and interposed between the perimetric frame 8 of the door 3 and the edge 9 of the opening 2.

It should further be noted that, in the embodiment defined above, the perimetric edge 9 of the opening 2 comprises respective slots 10 for accommodating the gaskets 4 and 5.

The gaskets 4 and 5, in the inactive configuration, therefore with minimum space occupation, can conveniently be contained within the slots 10; when on the other hand the gaskets 4 and 5 are in the expanded configuration, therefore with maximum space occupation, they will be protruding at least partially from the slots, and will therefore be in hermetic abutment against the perimetric frame 8 of the door 3.

According to an alternative embodiment that is equally advantageous in terms of implementation, the door 3 can oscillate with respect to the opening 2 and is adapted to enter inside it, substantially with a snug fit.

In this case the door 3 will define, with respect to the opening 2, a first configuration of juxtaposition and closure of the opening 2, at which the perimetric outline of the door 3 will effectively be aligned with and proximate to the edge of the opening 2.

In this embodiment the expandable gaskets 4 and 5 will be arranged, side by side, substantially along the inner walls of the opening 2, and interposed between the perimetric outline of the door 3 and the inner walls of the opening 2.

With particular reference to such embodiment, the inner walls of the opening 2 will comprise respective recesses for accommodating the gaskets 4 and 5.

The gaskets 4 and 5 in such case, in the inactive configuration, therefore with minimum space occupation, will be contained within the recesses, while in the expanded configuration, therefore with maximum space occupation, will protrude at least partially from the recesses, in hermetic abutment against the perimetric outline of the door 3.

With particular reference to an embodiment that enables an optimal operation of the packaging system, by defining the continuity of the conveyance path of the containers C between the apparatus A and the machine B and, at the same time, making it possible to interrupt such continuity simply and rapidly, the closing element 1 is controlled by an interconnection bridge 6 arranged along the conveyance path of the containers C from the sterilization apparatus A to the filling machine B.

The bridge 6 can move between an active arrangement for alignment with the portion of the conveyance path that is inside the apparatus A and is terminal with respect to it, and with the portion of the conveyance path that is inside the machine B and is initial with respect to it.

Figure 6:
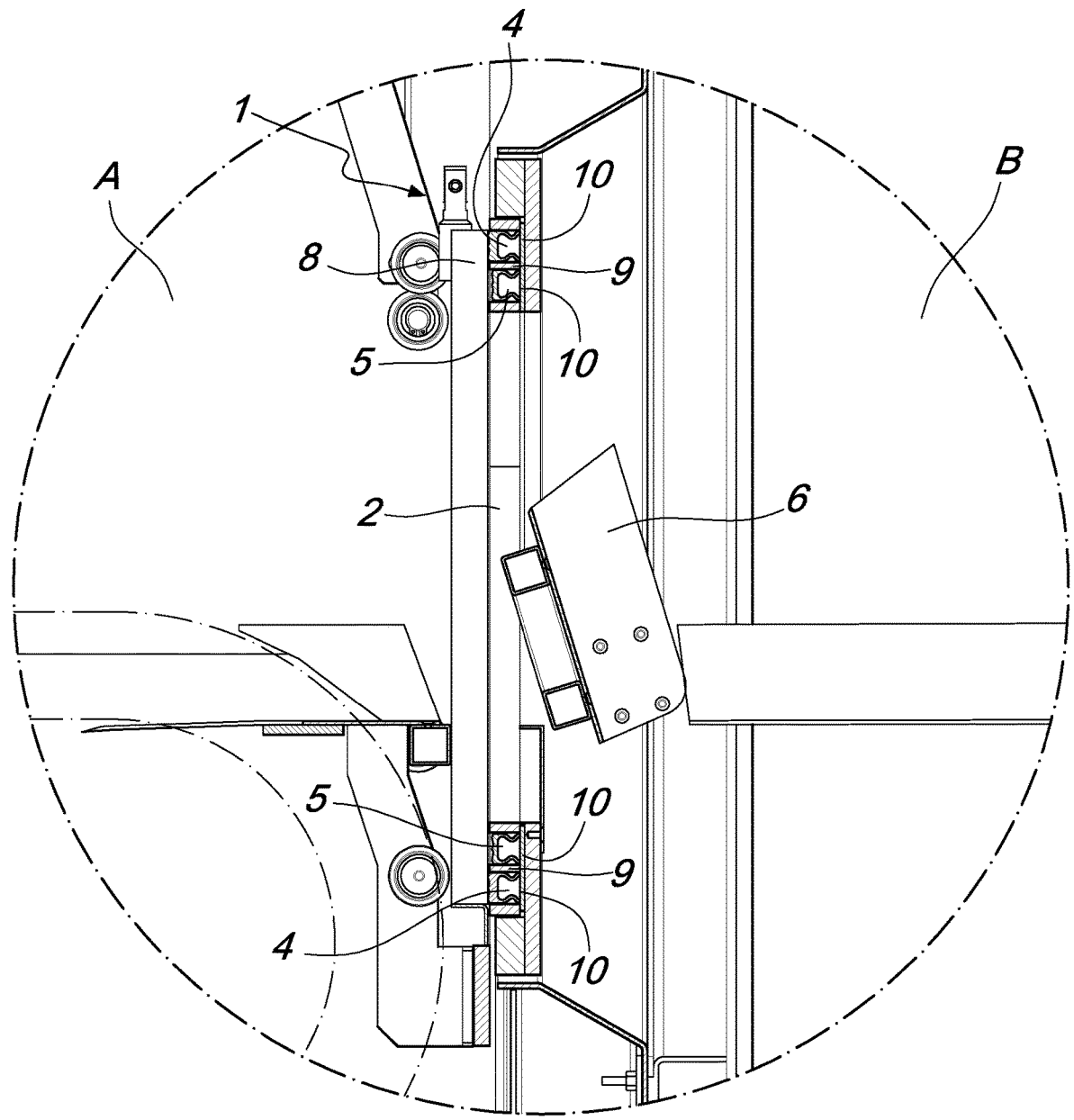
FIG. 6 is a schematic cross-sectional side view taken along a transverse plane of the step of closing the opening between a sterilization apparatus and a filling machine in order to carry out the sterilization of the filling machine.

The bridge 6 constitutes a guiding gangway for the containers C in transit, and also defines an arrangement of interrupting the path, when it is substantially misaligned with respect to such portions of the apparatus A and of the machine B (such as for example shown in FIGS. 1, 5 and 6).

Advantageously the aim of the present disclosure is to solve the above mentioned drawbacks, by providing a process of sterilization of a packaging system (constituted by a sterilization apparatus A and by a filling machine B) that is extended to all the parts and the components facing the conveyance path of the containers C.

As seen previously, all the parts of the packaging system will be subjected to sterilization by adopting the process according to the disclosure.

Positively the present disclosure also relates to an element 1 for closing the interface opening 2 between an apparatus A for sterilizing containers C and a filling machine B that makes it possible to subject every part of the apparatus A and of the machine B to sterilization operations and, in particular, the entire surface of the edges 9 delimiting the opening 2.

Conveniently the closing element 1 according to the disclosure enables the execution of extraordinary sterilization operations of the apparatus A and of the machine B in the traditional manner, that is, without it being necessary to execute further steps or to adopt external machines in order to ensure the correct sterilization also of the interface area between the apparatus A and the machine B. It is in fact sufficient to use the expandable gaskets 4 and 5 in order to ensure the completeness of the sterilization, by exploiting the possibility to expand them independently during the sterilization of the apparatus A and of the machine B.

Positively the element 1 for closing the opening 2 has a shape, a technical structure and an operation that are substantially different from those of conventional packaging systems, and therefore is original and innovative with respect thereto.

Conveniently the sterilization process according to the disclosure and the closing element 1 according to the disclosure can be implemented relatively simply and at substantially low cost: such characteristics make the described technical solutions easy and safe to practically apply.

The disclosure thus conceived is susceptible of numerous modifications and variations, all of which are within the scope of the appended claims. Moreover, all the details may be substituted by other, technically equivalent elements.

In the embodiments illustrated, individual characteristics shown in relation to specific examples may in reality be interchanged with other, different characteristics, existing in other embodiments.

In practice, the materials employed, as well as the dimensions, may be any according to requirements and to the state of the art.

The disclosures in Italian Patent Application No. 102016000027985 (UA2016A001756) from which this application claims priority are incorporated herein by reference.

The invention claimed is:

1. A process of sterilization of a packaging system, constituted by an apparatus for sterilizing containers and by a filling machine, the sterilization process includes the following steps:
   arranging a door so as to close an interface opening defined between said apparatus for sterilizing containers and said filling machine, first and second independently expandable gaskets, being interposed between said door and said opening on the same side with respect to the door and coupled to a perimetric region of a component chosen from either said door or a delimiting edge of said opening,
   subjecting said sterilization apparatus to sterilization, keeping inactive, therefore with minimum space occupation and separated from said door, the first gasket and keeping expanded, therefore with maximum space occupation and in hermetic abutment against said door, the second gasket, and
   subjecting said filling machine to sterilization, keeping inactive, therefore with minimum space occupation and separated from said door, the first gasket and keeping expanded, therefore with maximum space occupation and in hermetic abutment against said door, the second gasket.

2. The sterilization process according to claim 1, wherein said expansion of said first and second gaskets is obtained by way of an independent inflation thereof.

3. The sterilization process according to claim 1, further comprising a preliminary step of interrupting a conveyance path of said containers from said sterilization apparatus to said filling machine, which includes removing an interconnection bridge that is arranged between a first portion of said conveyance path that is inside said apparatus and a second portion of said conveyance path that is inside said machine.

4. A closure element for closing an interface opening between an apparatus for sterilizing containers and a filling machine, the closure element comprising a door, which can move between a first configuration of juxtaposition and closure of said opening and a second configuration of misalignment and opening of said opening, between said door and an edge of said opening, and juxtaposed therewith in said first configuration, there being interposed on the same side with respect to the door and coupled to a perimetric region of a component chosen from either said door or a delimiting edge of said opening at least two continuous and closed perimetric gaskets, which delimit said opening, each gasket being expandable independently, upon an expansion of at least one first gasket, at least one second gasket, not subjected to expansion, being connected to an internal compartment of either said sterilization apparatus or said filling machine, therefore undergoing a sterilization treatment simultaneously with the respective compartment.

5. The closure element according to claim 4, wherein said expandable gaskets are of the type that can be inflated by way of a respective pneumatic supply circuit which is controlled by a respective control and management unit.

6. The closure element according to claim 4, wherein said door can slide parallel to said opening, in the first configuration of juxtaposition and closure of said opening, a perimetric frame of said door being aligned and proximate to a perimetric edge of said opening, one of said expandable gaskets inscribing the other, and arranged substantially along a perimeter of said opening and interposed between said perimetric frame of said door and said perimetric edge of said opening.

7. The closure element according to claim 6, wherein said perimetric edge of said opening comprises slots for accommodating said gaskets, said gaskets, in an inactive configuration, therefore with minimum space occupation, being entirely contained within said slots, and in an expanded configuration, therefore with maximum space occupation, protruding at least partially from said slots, in hermetic abutment against the perimetric frame of said door.

8. The closure element according to claim 4, wherein said door can oscillate with respect to said opening and is adapted to enter inside it, substantially with a snug fit, in the first configuration of juxtaposition and closure of said opening a perimetric outline of said door being aligned with and proximate to the perimetric edge of said opening, said expandable gaskets being arranged, side by side, substantially along inner walls of said opening, and interposed between a perimetric frame of said door and the inner walls of said opening.

9. The closure element according to claim 8, wherein the inner walls of said opening comprise respective recesses for accommodating said gaskets, said gaskets, in an inactive configuration, therefore with minimum space occupation, being entirely contained within said recesses, and in an expanded configuration, therefore with maximum space occupation, protruding at least partially from said recesses, in hermetic abutment against the perimetric frame of said door.

10. The closure element according to claim 4, further comprising an interconnection bridge that is arranged along a conveyance path of said containers from said sterilization apparatus to said filling machine, said bridge being movable between an active arrangement of alignment with a first portion of said conveyance path that is inside said apparatus and with a second portion of said conveyance path that is inside said machine, constituting a guiding gangway for said containers in transit, and an arrangement of interrupting the path, in which it is substantially misaligned with respect to said first and second portions of said apparatus and said machine.

\* \* \* \* \*